United States Patent
Mumme et al.

(10) Patent No.: US 8,945,892 B2
(45) Date of Patent: Feb. 3, 2015

(54) PROCESS AND DEVICE FOR CONTINUOUS LIQUEFACTION OF ORGANIC SOLIDS

(75) Inventors: Jan Mumme, Berlin (DE); Bernd Linke, Potsdam (DE); Rainer Toelle, Berlin (DE)

(73) Assignee: Leibniz-Institut fuer Agrartechnik Potsdam-Bornim E.V. (ATB), Potsdam (DE)

( * ) Notice: Subject to any disclaimer, the term of this patent is extended or adjusted under 35 U.S.C. 154(b) by 1752 days.

(21) Appl. No.: 12/224,110

(22) PCT Filed: Oct. 23, 2006

(86) PCT No.: PCT/DE2006/001891
§ 371 (c)(1), (2), (4) Date: Dec. 10, 2008

(87) PCT Pub. No.: WO2007/093138
PCT Pub. Date: Aug. 23, 2007

(65) Prior Publication Data
US 2009/0305377 A1    Dec. 10, 2009

(30) Foreign Application Priority Data
Feb. 16, 2006 (DE) .......................... 10 2006 008 026

(51) Int. Cl.
| C12P 1/02 | (2006.01) |
| C12M 1/107 | (2006.01) |
| C02F 11/04 | (2006.01) |
| C05F 17/02 | (2006.01) |
| C12M 1/16 | (2006.01) |

(Continued)

(52) U.S. Cl.
CPC ............ *C02F 11/04* (2013.01); *C05F 17/0247* (2013.01); *C12M 21/04* (2013.01); *C12M 21/16* (2013.01); *C12M 23/58* (2013.01); *C12M 29/02* (2013.01); *C12M 33/14* (2013.01); *C12M 33/16* (2013.01); *C02F 3/286* (2013.01); *Y02E 50/343* (2013.01)
USPC ....... 435/167; 435/41; 435/290.4; 435/290.2; 435/168; 435/286.6; 435/286.7; 435/289.1

(58) Field of Classification Search
None
See application file for complete search history.

(56) References Cited

U.S. PATENT DOCUMENTS 2,335,562 A * 11/1943 Downes .................... 210/120

(Continued)

FOREIGN PATENT DOCUMENTS

| EP | 0 033 017 A1 | 8/1981 |
| ZA | 200002826 A * | 3/2001 |

OTHER PUBLICATIONS

Linke et al., "Ergebnisse aus den wissenschaftlichen Begleitungen der Pilotanlagen Pirow und Clausnitz," Trockenfermentation—Stand der Entwicklungen und Weiterer F+E-Bedarf, vol. 24, pp. 112-130 (Feb. 4, 2006).

*Primary Examiner* — Jon P Weber
*Assistant Examiner* — Aaron J Kosar
(74) *Attorney, Agent, or Firm* — Kriegsman & Kriegsman

(57) ABSTRACT

A method for the continuous liquefying of organic solids in a fermenter, wherein an outwardly directed flow of solids is produced in a dammed-up liquid, the solids are added in the lower region of the fermenter and the solid fermentation residues are essentially collected and removed below the level of the dammed-up liquid.

14 Claims, 6 Drawing Sheets

Figure 1:
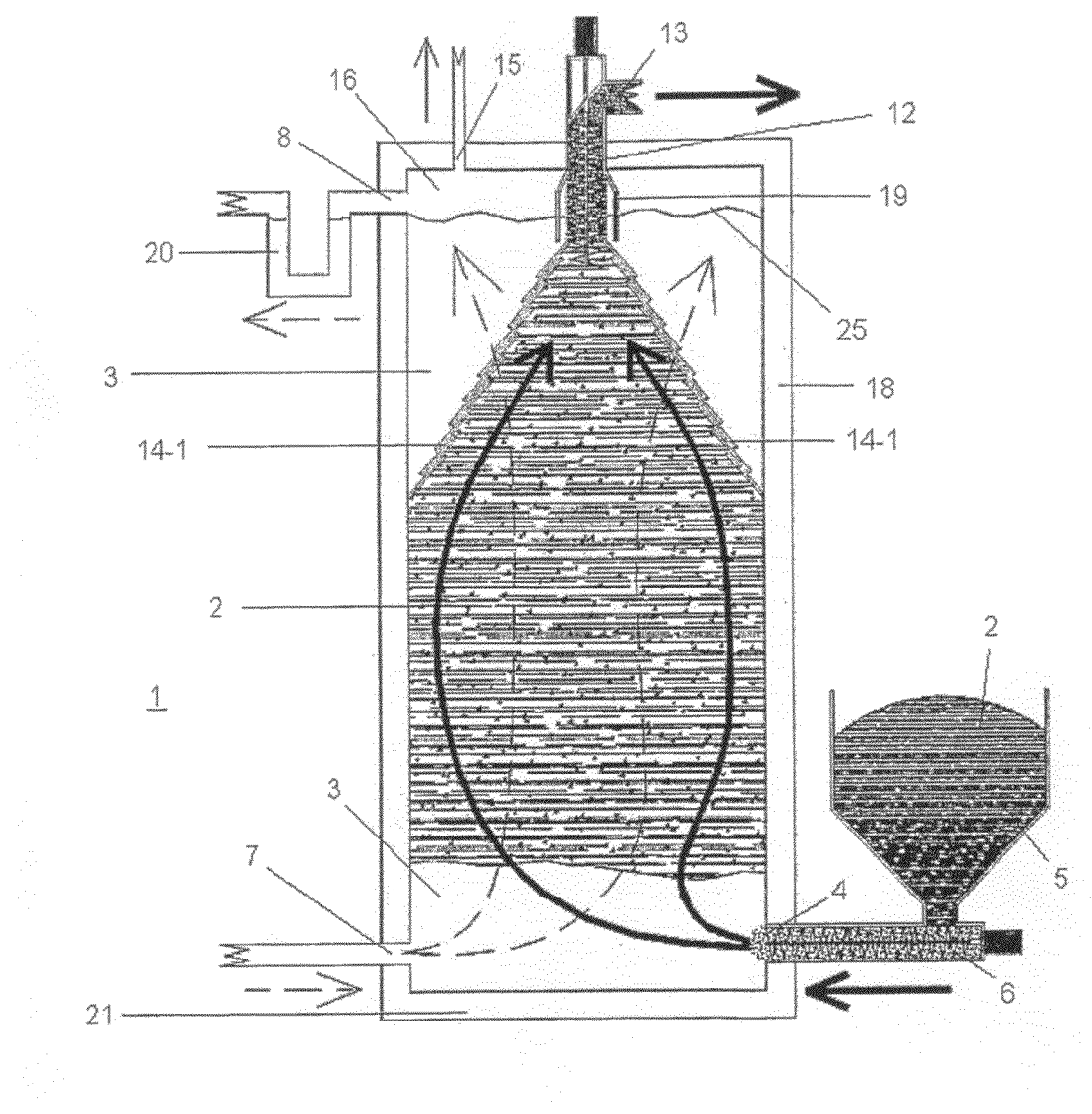

(51) Int. Cl.
*C12M 1/26* (2006.01)
*C12P 1/00* (2006.01)
*C12M 1/00* (2006.01)
*C12M 1/02* (2006.01)
*C12P 3/00* (2006.01)
*C02F 3/28* (2006.01)

(56) References Cited

U.S. PATENT DOCUMENTS 3,617,541 A * 11/1971 Pan .............................. 210/615
4,036,754 A * 7/1977 Peasley ........................ 210/139
5,553,534 A * 9/1996 Soavi .......................... 100/145

* cited by examiner

PROCESS AND DEVICE FOR CONTINUOUS LIQUEFACTION OF ORGANIC SOLIDS

The invention relates to a method and a device for the continuous liquefying of organic solids as well as the use of the device.

Organic solids are almost exclusively fermented in biogas plants, which were developed originally only for the treatment of liquid substances (agitated boiler-fermenter), based on the principle of complete intermixing. Considerable disadvantages result in conducting the process and also relative to the energy requirement in producing biogas, when organic solids are used in intermixing biogas plants. The high energy content and the small buffering capacity of the solid biomass involve the latent danger of an overloading and a disruption of the biogas process. In order to prevent the automatic demixing of solids in the fermenting liquid, high quantities of energy must also be used for homogenization by means of stirring mechanisms or pumps.

The so-called method of dry fermenting was developed with the objective of providing an advantageous method for the fermentation of solids. Methods of dry fermenting can be divided into discontinuous and continuous operating modes. While discontinuous methods which can be applied in boxes, foil-covered pits or in containers possess the disadvantage of a productivity that fluctuates greatly over time, continuous methods for which fermenting channels and vertical silos are used are technically very expensive to implement.

In conventional agitated boiler-fermenters, a floating mass of solids is considered disruptive. This is based on the danger of a local disruption of the process due to over-acidifying and drying out as well as hindering the biogas discharge. This is counteracted by intensive homogenization by means of pumps or stirring mechanisms.

The object of the present invention is to provide a simple implementation in terms of plant and process technology for the continuous liquefying of organic solids.

The object of the present invention is accomplished by a method, in which an outwardly directed flow of solids is produced in a dammed-up fluid, wherein the solids are added in the lower region of the fermenter and the solid fermentation residues are collected and removed essentially below a liquid surface level of the dammed-up fluid. Gaseous reaction products, the fermentation gases, are removed in the upper region of the fermenter, while dissolved organic substances may also be removed at other positions.

The liquid in the dammed-up fluid essentially involves water, which is enriched with residual substances of the fermentation such as, for example, cell fluid, in the course of the dry fermentation process.

The fermentation gases essentially involve carbon dioxide, methane, hydrogen and hydrogen sulfide. Oxygen, if it enters the fermenter, is swiftly consumed.

For example, biowaste, grass cuttings, industrial wastes, food wastes, agricultural wastes, kitchen wastes, organic wastes or washed-out raw materials and similar substances are introduced into the fermenter as organic solids.

The solid fermentation residues are collected in the upper region of the fermenter. The collecting is carried out by sieves which are introduced below a liquid surface level of the dammed-up fluid or are found at least only at a short distance above the liquid surface level of the dammed-up fluid. The sieves are thus shaped like funnels, so that the solid fermentation residues can be introduced for their removal.

The invention combines in a simple and energetically favorable manner the advantages of a continuous operating mode with the advantages of dry fermentation.

The method of the present invention involves a continuous dry fermentation method. While in a wet fermentation, the content of the fermenter usually has a water content of more than 90%, dry fermentation methods operate with an average content of dry substance above 10% in the fermenter. Biomass that can be stacked can be fermented in a wet fermenter. A deciding factor here is the water content in the fermenter.

Conducting a discontinuous method as compared to a continuous method is essentially distinguished by the fact that in the discontinuous method, the biomass is introduced by batches, while in the continuous method, the biomass is introduced by through-flow. This continuous operating mode has the advantage that a uniform productivity can be achieved.

Additional advantages of the method according to the invention are the high productivity and stability of the fermentation process due to the high concentrations of degradable solids and solid buffer substances in the fermenter and the simple, compact structural design of the fermenter.

The method of the present invention makes it possible to design the continuous dry fermenting of solids for the production of energy-rich liquid and/or gaseous decomposition products with little expenditure for process technology. In this case, the residence time of the biomass can be adjusted by the selection of suitable process parameters.

The optimal residence time of organic solids is dependent on the application objective of the fermenter, the type of solids used and the reaction conditions in the fermenter. The optimal residence time for solids lies approximately in a range of 3 to 28 days.

Organic solids can be liquefied in high concentration with the method of the present invention. This means that the process throughput for solid fermentation is increased. In known intermixing wet fermentation methods, there is a daily throughput of approximately 2-4 kg of organic dry substance per cubic meter of fermenter space. Throughputs of 10 kg/m$^3$ per day or more, thus more than double the amount, can be achieved by the continuous, non-intermixing liquefying of the solids according to the method of the invention.

The throughput of solids with standard intermixing fermentation methods is limited by the fact that too large an addition of solids leads to an over-acidification in the fermenter, whereupon there is a strong inhibition of the bacteria that participate in the process.

An advantage of the method according to the invention is that such an over-acidification does not occur due to the liquefying of solids and the discharge of dissolved decomposition products that is made possible in this way, and thus a higher throughput can be achieved.

The throughput of solids in the method according to the invention is only limited by the actual conditions of the technical plant; in principle, even 100 kg/m$^3$ per day is possible. The yield, thus the rate or percent of liquefying, is dependent on biological and chemical factors. The potentially obtainable liquefying rate is very dependent on the type of solids used. Relative to the mass of organic dry substance, the liquefying rate is not basically different in dry and wet fermenters. The advantage results due to the higher concentration of solids in the fermenter. At least 50% higher concentrations of dry substance are possible.

If one would like to obtain a higher yield, one can operate a two-step method, in order to convert the reaction products obtained in the first step (liquid in the dammed-up fluid, solid fermentation residues, fermentation gases) into the desired final products, for example, biogas, in a targeted manner in another fermenter.

A continuous intermixing of the material is not required, since the method according to the invention makes use of the tendency of the biomass to form floating layers. The method thus utilizes the floating of the organic solids that occurs naturally for transport of the solids in the fermenter. The floating is brought about by layering fermentation gas bubbles on the solid particles and is called flotation. There arises an outwardly directed flow of droplets with an upwardly increasing density gradient. This has the advantage that there is only a small energy requirement for the process due to the lack of homogenization needed for the solid reactor contents and the utilization of natural solid flotation for moving the solids.

In contrast to the conventional method in agitated boiler-fermenters, an outwardly directed flow of solids is produced in the fermenter in the method according to the invention. A continuous operating mode of the fermenter is made possible in this way. The utilization of spontaneous flotation of solids also represents an energetically favorable transport method.

The layering density of the solids to be fermented is dependent on the type of solids and can reach local maximum values of up to 0.8 $t/m^3$ in the fermenter. The layering density basically increases toward the top. A zone almost free of solids is formed in the lower region. On average, a density of 0.3 to 0.5 $t/m^3$ is expected.

The proportion of dry substance in the content of the fermenter increases toward the top and can reach a value of up to 50 wt. %. On average, a content of dry substance between 10 and 20 wt. % is expected.

For the case when the solids fermenter will be used for methane production, a process temperature in the (dry) fermenter between 35 and 42° C. or 50 and 65° C. is the most favorable. Mesophilic or thermophilic methane bacteria have their preference region in this range. If the solids fermenter will be used primarily only for liquefying solids, temperatures of up to 95° C. can also be adjusted. Hydrolytically active extremophiles (65-85° C.) and hyperthermophiles (>85° C.) possess their temperature optima in this region. In addition to an acceleration of the decomposition process, these temperatures also make possible an effective sanitization of the solids as well as a reliable inactivation of weed seeds.

The pH in the solids fermenter can lie locally between 3.5 and 8.5. The pH increases toward the top. If methane is to be formed in the solids fermenter, it is favorable to produce fermenter zones with neutral pH (6.5 to 7.5) that are as large as possible. pH values between 5.2 and 6.3 are favorable for the liquefying of solids without formation of methane.

Anaerobic conditions are necessary for methane formation.

The C/N ratio should lie between 20:1 and 30:1 for methane formation and between 10:1 and 45:1 for the liquefying of solids.

The solids are preferably introduced below the liquid surface level in the fermenter of the fermenter. It is assured by this structure of the method of the invention that the rising solids are essentially found below the liquid surface level. In this way, a drying out and a disruption of the outflow of fermentation gases are prevented. The intermediate products of the decomposition remain mobile, whereupon a local disruption of the process due to an inhibition of the products is avoided.

A flow of droplets of solids to fermenting organic substances is produced in the fermenter. New solids are added in the lower region of the fermenter and solid fermentation residues are removed in the upper region. The addition of solids to the fermenter is carried out by active conveying means.

In a preferred embodiment of the invention, the solids are introduced into the fermenter via a liquid-impermeable conveyor device. In this way, the solids are introduced into the fermenter via a liquid-impermeable feed screw conveyor from a substrate storage basin through a channel, which passes horizontally through the wall of the fermenter.

The solids can also be added, however, via liquid-permeable conveyor devices.

In another preferred embodiment of the invention, the solids are introduced into the fermenter via a conveyor device which has a conveyor path segment that begins above the liquid level of the fermenter. The use of a feed screw conveyor is offered for this purpose. Immersed pipes or shafts reaching to the lower region of the fermenter can be used as the feed path segment. These pipes or shafts can be disposed both inside as well as outside the fermenter.

In another preferred embodiment, the solids are introduced into the fermenter by mechanical, hydraulic or pneumatic conveying methods. The hydraulic or pneumatic conveying methods can thus be utilized alternatively or in a supporting manner for the mechanical conveyance of solids. liquid in the dammed-up fluid and/or fermentation gas can be used as a transport medium.

In another preferred embodiment of the invention, the solids are spread out in the lower region of the fermenter. The solids can be spread out in the lower region by the most varied methods; thus, for example, a flow can be produced by means of introducing the liquid or the fermentation gases. Another possibility is the use of a stirring mechanism.

The solid fermentation residues are preferably removed with a pressure and/or a feed screw conveyor. This is carried out in the upper region of the fermenter, for example, at the top of the fermenter. The pressure and feed screw conveyors are combined with one another in this case.

Further, the pressure and/or feed screw conveyor can be coupled with the stirring mechanism via a shaft. The stirring mechanism will only be moved slowly due to the coupling, since removal will be possible also only at slow speed. The coupling can thus exclude the circumstance that there will be a disruption of the layer of solids due to too strong a swirling of the solids in the dammed-up liquid.

The removal of the solid fermentation residues by a combined pressure and feed screw conveyor has the advantage that the liquid that is pressed out remains in the fermenter. An impermeability to gas is attained by the solids droplets that form in the screw conveyor. There are other possibilities also, however, for the removal of solid fermentation residues.

In another preferred embodiment of the invention, the solid fermentation residues are guided by a solids scraper into a downpipe or a shaft. As an alternative to the removal of the solid fermentation residues directed toward the top, a discharge can be carried out toward the bottom by means of a downpipe or shaft. These downpipes or down shafts can be disposed both inside as well as outside the fermenter. In order to obtain the necessary impermeability to gas, a liquid-filled siphon or an immersed device is introduced in the lower region of the downpipe or down shaft. The displacement of the solid fermentation residues into the downpipe or into the shaft can be accelerated by a rotating solids scraper.

In yet another preferred embodiment of the invention, an underpressure is produced at the position where the solid fermentation residues are removed. By applying an underpressure at the position where the solids are removed, the buoyancy of the mass of solids can be increased. In this way a further increase of the density gradient is achieved, whereby the separation of the solid and liquid substance phases can be accelerated.

The fermentation gases and the liquid are preferably separated from the solids in the dammed-up fluid sieving. In this case, the sieves are utilized simultaneously for holding down the solids. The separation of the fermentation gases from by sieving surfaces in the middle and lower regions can be improved by the device.

The liquid in the dammed-up fluid, parts of the solid fermentation residues and/or parts of the fermentation gases are preferably circulated through the fermenter or through several fermenters. By means of the circulation of the liquid in the dammed-up fluid and/or the fermentation gases, these can be used, for example, as means for hydraulic or pneumatic conveyance. It is also possible to transfer the liquid and/or the solids to another fermenter. The liquid and/or the solids can be returned to the first fermenter from this second fermenter or can be withdrawn from the circulation.

In order to further increase the process performance and the stability of formation of fermentation gases, in addition to the dammed-up fluid, solid fermentation residues can also be returned to the fermenter. The increase in process performance and stability is principally based on the recycling of the required microorganisms as well as acid-buffering substances.

The dammed-up fluid is preferably transferred from the fermenter into a second fermenter and from there back again into the first fermenter. A further increase in the process stability and performance can be made possible by the combination of the fermenter with a separate methanation reactor for the treatment of the dammed-up fluid. For this purpose, the dammed-up fluid is conducted from the fermenter into the methanation reactor and from there back again into the fermenter.

The dammed-up fluid and/or the solid fermentation residues is/are preferably transferred from the fermenter into a second fermenter, whereby a fermentation gas containing methane and/or hydrogen is produced in the second fermenter, and this gas can be returned again if needed to the first fermenter. In order to increase the throughput, the precursors of the biogas production are produced in the first fermenter and these are then converted to biogas in a second fermenter. For this purpose, the proportion of methane is increased in the fermentation gas in the second fermenter.

The fermentation gas produced in this way in the second fermenter can either be removed from the process or can be transferred again into the first fermenter.

The solid fermentation residues are preferably removed from the fermenter and transferred back again into the fermenter or they are conducted from the fermenter into a second fermenter. The solid fermentation residues can thus be returned directly to the same fermenter. In this way, the solid fermentation residues can be introduced again as solids into the fermenter. Another possibility consists of the fact that the solid fermentation residues can be post-treated in a second fermenter. The solids that are fed back, however, can also be used for the initial seeding of a dry fermenter, whereby the starting phase of the fermentation process can be accelerated.

Enzymes, microorganisms and/or trace elements are preferably introduced into the fermenter. Another acceleration of the process due to such use of enzymes or microorganisms is possible, since the organic solids can be more rapidly decomposed.

The addition of the following substances can be useful: air, fermentation gases, enzymes, acid buffers, trace elements and/or microorganisms.

Air can accelerate the liquefying of the solids, but prevents methane formation.

Fermentation gases serve for increasing the buoyancy of the solids for the vortexing of the sedimentation sludge at the bottom of the fermenter and for equilibrating the solids content in the lower region of the fermenter.

Cellulases, hemicellulases, lipases, proteases and/or amylases can be added as enzymes.

Buffers based on calcium or ammonium, for example, can be used as acid buffers.

Nickel, cobalt, molybdenum, selenium and/or tungsten can be added as trace elements. Methane bacteria, in particular, have a high requirement for trace elements.

Microorganisms can be added from other fermentation plants, for example, in the form of liquid or solid seeding material, in particular, for the acceleration of the start-up phase.

In addition, the object of the present invention is accomplished by a liquefying plant, wherein the fermenter contains at least one liquid discharge outlet, at least one sieve, as well as
at least one solids inlet and one liquid inlet in the lower region and
at least one discharge outlet for fermentation residues and one discharge outlet for gas in the upper region.

The organic solids are mixed with the dammed-up fluid in the lower region of the fermenter. Due to the fermentation process, the solids float up and are collected by a sieve and are discharged in the upper region of the fermenter. The solid fermentation residues are separated from the fermentation gases and the liquid from the dammed-up fluid by the sieve. The fermentation gases and the dammed-up liquid are discharged from the fermenter through a gas or liquid discharge outlet in the upper region of the fermenter. It is also possible, however, to conduct the liquid discharge at other places. For example, a horizontal liquid flow with laterally introduced inlets and outlets would also be conceivable.

The fermentation gases removed from the fermenter can be guided back again into the fermenter. The fermenter thus preferably has at least one gas inlet. It is also possible, however, to introduce fresh gases, which do not originate from fermentation processes, into the fermenter. For example, the intermixing of solids and the liquid in the dammed-up fluid can be promoted in this way.

In a preferred embodiment of the invention, a liquid-impermeable conveyor device is disposed at the solids inlet of the fermenter. In this way, the solids can be introduced underneath the liquid surface level of the fermenter. Further, it is possible to adjust the proportion of solids in the fermenter in a targeted manner.

In another preferred embodiment of the invention, a conveyor device is introduced at the solids inlet of the fermenter, whereby the beginning of the conveyance path is disposed above the liquid surface level of the fermenter. In this embodiment, for example, a feed screw conveyor can be used for loading the fermenter with solids. Immersed pipes or shafts that reach down to the lower region of the fermenter can thus be used as the conveyance path, whereby these pipes or shafts can be disposed both inside as well as outside the fermenter.

In yet another embodiment, a device for the mechanical, hydraulic or pneumatic conveyance of the solids is preferably disposed at the solids inlet of the fermenter. The liquid or fermentation gases which are pumped in a circuit through the fermenter can be used as the transport medium.

The discharge outlet [means] for the fermentation residues of the fermenter is preferably a pressure and/or feed screw conveyor. The discharge outlet for the fermentation residues should be introduced in the upper region of the fermenter, for example, centrally on the top of the fermenter. The pressedout the liquid from the dammed-up fluid thus remains in the fermenter. Gas impermeability is achieved by the droplets of solids that form in the screw. An optimization of the impermeability to gas can be achieved by immersing a sleeve that surrounds the discharge outlet for the fermentation residues.

In another preferred embodiment of the invention, the discharge outlet for the fermentation residues of the fermenter is formed in a downpipe or down shaft, wherein a liquid-filled siphon or an immersed device is introduced in the lower region of the downpipe or down shaft.

The discharge outlet for the fermentation residues of the fermenter preferably has a rotating solids scraper, which conveys the solid fermentation residues into the downpipe or the shaft.

An underpressure can preferably be generated at the discharge outlet for the fermentation residues. This underpressure can be generated by pumps. The outwardly directed flow of the solids will also be accelerated by the underpressure.

A stirrer is preferably accommodated on the bottom of the fermenter. In this way, the newly introduced solids can be spread out uniformly in the fermenter. The rising layer of solids, however, is no longer stirred.

Further preferred, the pressure and/or feed screw conveyor of the discharge outlet for the fermentation residues of the fermenter and the stirrer are coupled. Due to the slow movement of the feed screw conveyor, the stirrer is also moved only at a slow speed, which is just sufficient to intermix the newly introduced solids and the dammed-up liquid, but does not lead to a vortexing of the solids that have already risen to the top and also does not adversely affect the further floating up of the solids.

The fermentation gases and the liquid in the dammed-up fluid are separated from the solids through a sieve in the upper region of the fermenter.

The sieve of the fermenter is preferably funnel-shaped. In this way an automatic movement of the solids or the solid fermentation residues is produced in the direction of the discharge outlet for the fermentation residues.

The sieve consists of obliquely disposed lamellae that prevent a clogging of the sieve openings. Preferably, additional sieve surfaces are disposed in the middle and lower regions of the fermenter, whereby an improved separation of the fermentation gases is achieved.

The liquid in the dammed-up fluid and/or the solid fermentation residues can preferably be cycled from the fermenter through at least one other fermenter. One advantage of a separate treatment of the the liquid from the dammed-up fluid in a second fermenter is that this fermenter can be designed especially for the decomposition of dissolved intermediate products. This makes possible a reduction of the concentration of organic acids in the fermenter. In this way, the risk of an over-acidification is counteracted and the loading of the fermenter with organic solids can be clearly increased. In the second fermenter especially designed for the decomposition of dissolved organic substances, extraordinarily high rates of biogas formation also can be achieved. In this way, the performance of the entire system can be considerably increased. Suitable types of fermenters for the decomposition of dissolved substances include, among others, solid-bed reactors and sludge-bed reactors.

In addition, the object of the present invention is attained by a use of the liquefying plant for the production of a fermentation gas containing methane and/or hydrogen. Depending on the solids introduced into the fermenter and the reaction conditions, the composition of the fermentation gas can be controlled during its production. Thus, the fermentation gas may contain an increased proportion of hydrogen and/or methane.

The method for the continuous liquefying of organic solids is used for the production of precursor products for biogas production. It is also possible, however, to use the method for the direct generation of biogas.

Further, the object of the present invention is achieved by a use of the liquefying plant for the production of organic acids which are dissolved and decomposed in at least one other fermenter for forming a fermentation gas containing methane and/or hydrogen The organic acids serve as precursors for the production of fermentation gases with an increased proportion of hydrogen or of methane.

In addition, the object of the present invention is attained by a use of the liquefying plant for removing germs from food wastes.

Also, a pasteurizing of food wastes can be carried out with the method.

Figure 2:
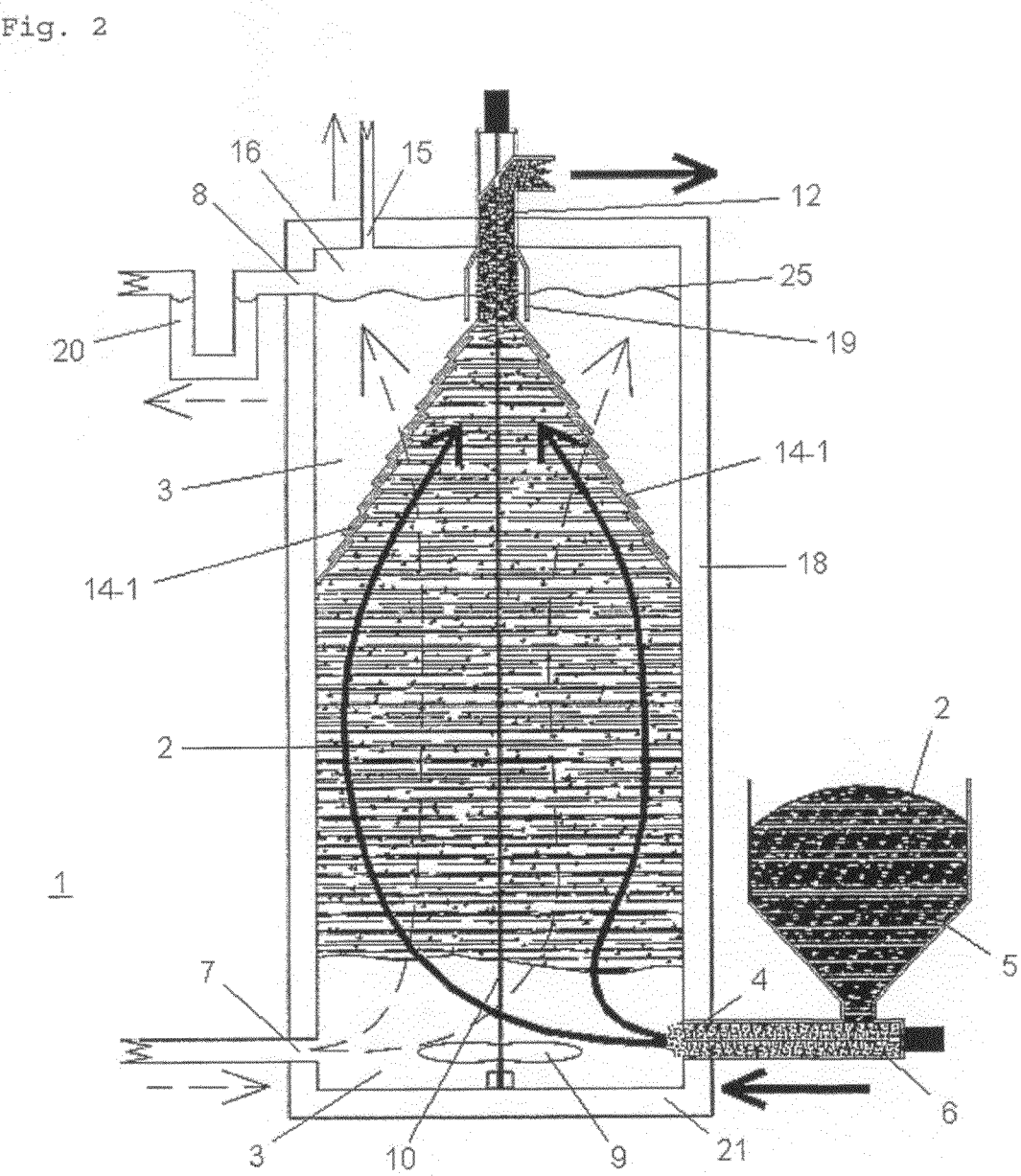
Figure 3:
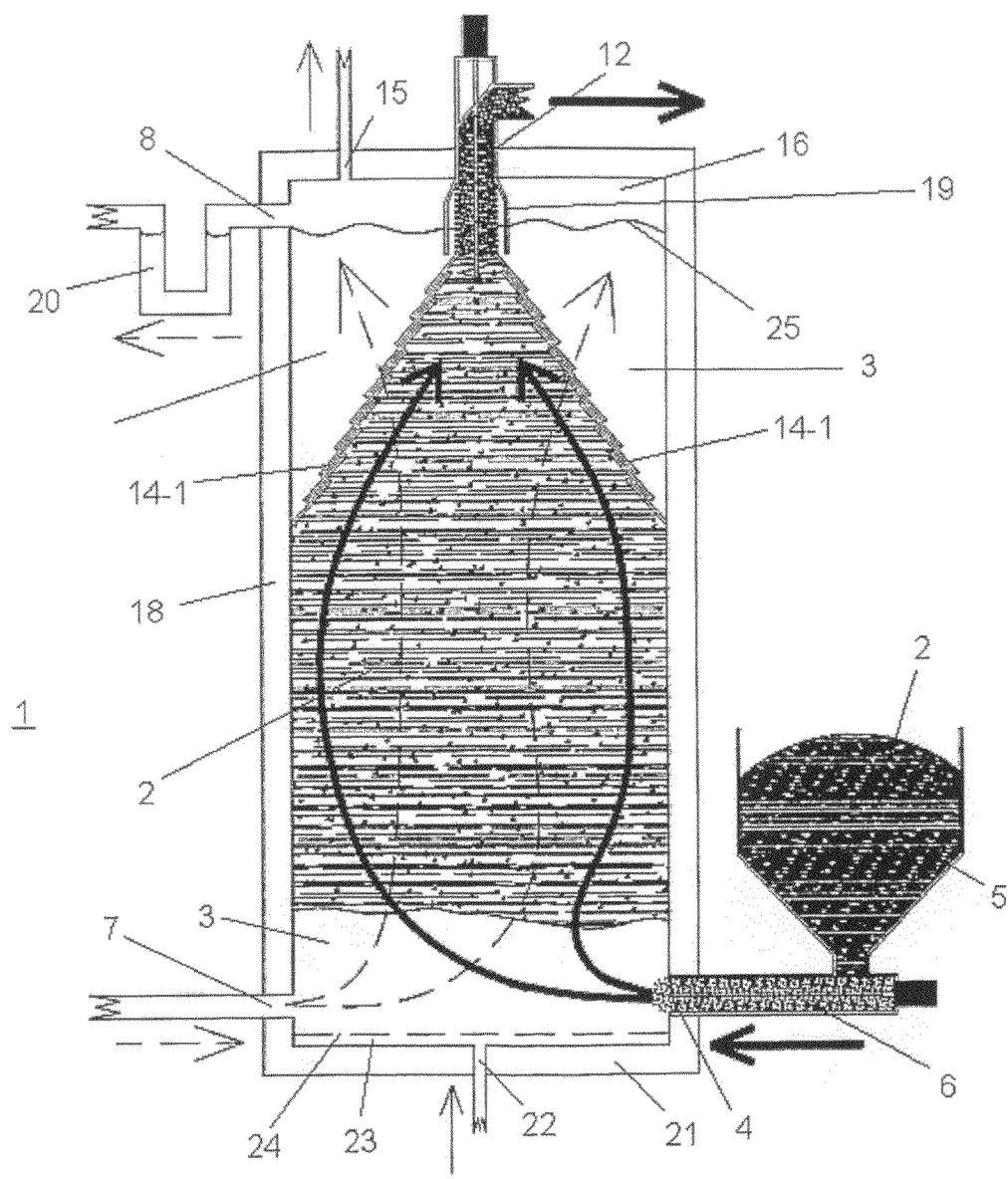
Figure 4:
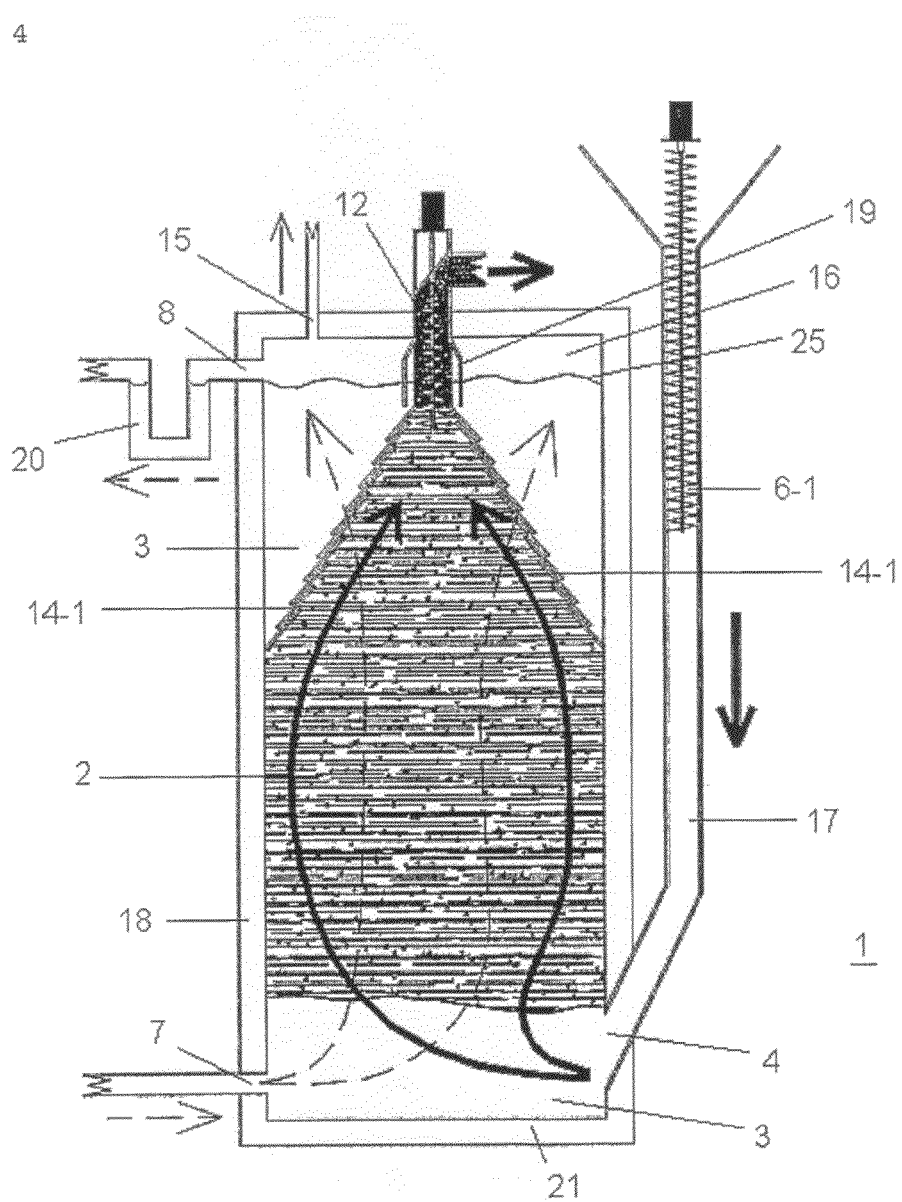
Figure 5:
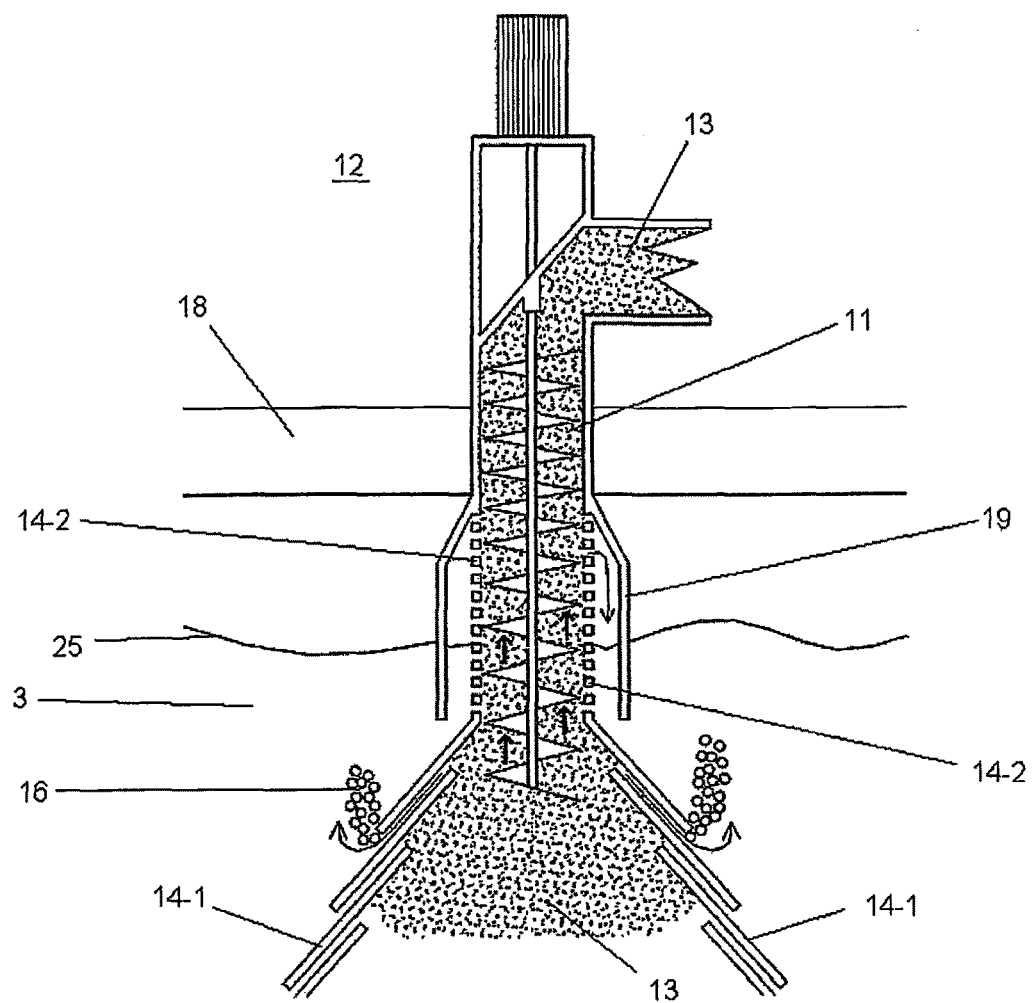
Figure 6:
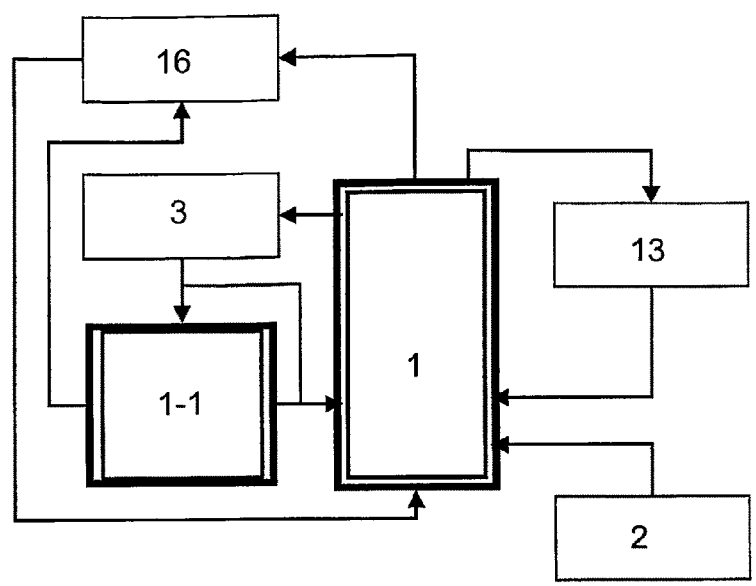

The invention is explained in detail in the following on the basis of the drawings. Taken individually, FIG. 1 shows a cross section through a fermenter, FIG. 2 shows a cross section through a fermenter with a stirring device, FIG. 3 shows a cross section through a fermenter with a gas inlet at the bottom of the fermenter, FIG. 4 shows a cross section through the fermenter with an inlet for solids via an immersed pipe lying outside, FIG. 5 shows a cross section through the discharge outlet for the fermentation residues, and FIG. 6 shows a schematic representation of a liquefying plant.

FIG. 1 shows a cross section through a fermenter 1 for the continuous liquefying of organic solids 2. The flow of solids 2 through fermenter 1 is shown in FIG. 1 by the thick arrows, the liquid flow of the liquid 3 in the dammed-up fluid is represented by the thin dashed arrows and the gas discharge is shown by the thin solid arrow.

Fermenter 1 has an inlet for solids 4 disposed in the lower region of fermenter 1. The organic solids 2 that are to be fermented are introduced into fermenter 1 from a solids storage container 5 via a conveyor device 6, for example, a feed screw conveyor 6-1. In addition, the liquid inlet 7, through which the dammed-up liquid 3 is introduced into fermenter 1, is accommodated in the lower region of fermenter 1.

The liquid 3 in the dammed-up fluid circulates through fermenter 1 by being introduced into fermenter 1 through the liquid inlet 7 and is discharged from fermenter 1 again through the liquid discharge outlet 8. An outwardly directed flow arises in fermenter 1 due to this circulation, by means of which the floating of solids 2 is supported. Fermentation gas 16 is not discharged at liquid discharge outlet 8; a siphon 20 is found at liquid discharge outlet 8.

FIG. 2 also shows a cross section through a fermenter 1 for the continuous liquefying of organic solids 2. In fermenter 1 which is shown in FIG. 2, however, a stirrer 9 is disposed on the bottom of the fermenter in order to improve the distribution of newly introduced solids 2.

This stirrer 9 is coupled via a shaft 10 to the pressure and feed screw conveyor 11 in the discharge outlet 12 for the fermentation residues.

The pressure and feed screw conveyor 11 serves for the simultaneous removal and drainage of the solid fermentation residues 13. A sieve 14 is accommodated under the pressure and feed screw conveyor 11. Liquid and gaseous components are separated by this lamella-shaped sieve with openings 14-1. Sieve 14 tapers like a funnel in the direction of pressure and feed screw conveyor 11, so that solids 2 are directly introduced into the pressure and feed screw conveyor 11 and thus the discharge outlet 12 for the fermentation residues.

A gas discharge 15, through which the fermentation gas 16 is discharged from fermenter 1, is found on the upper side of fermenter 1.

FIG. 3 shows a cross section through another embodiment of fermenter 1. Here, in the lower region of fermenter 1, an equilibration of the newly introduced solids 2 is made possible by a gas inlet 22 found on the bottom 21 of the fermenter. Gas is blown through the gas inlet 22 via gas distribution pipes 23 with openings 24, which are found on the bottom of fermenter 1. In this way also, solids that are collected on bottom 21 of the fermenter are again swirled with the liquid 3 in the dammed-up fluid. The vortexing takes place, however, in a way that does not adversely affect the floating of the solids.

FIG. 4 shows a fermenter 1 with another embodiment of the inlet for solids 2. In the embodiment shown in FIG. 4, solids 2 are introduced into the solids inlet 4 of fermenter 1 through an immersed pipe 17 that lies outside.

Solids inlet 4 is angled obliquely upward and therefore is not introduced horizontal to fermenter wall 18 as was the case in the embodiments shown in FIGS. 1 to 3.

FIG. 5 shows a detail view of fermenter 1 in cross section. FIG. 5 illustrates how fermentation gas 16 can escape through the openings of the lamella-type sieve with openings 14-1, whereas the solid fermentation residues 13 are introduced via pressure and feed screw conveyor 11 to the discharge outlet 12 for the fermentation residues (thick arrows: flow of solids). The liquid 3 from the dammed-up fluid can be discharged both through the openings of the lamella-type sieve with openings (shown by the thin arrows), as well as through a sieve 14-2 of the pressure and feed screw conveyor 11.

A sleeve 19 immersed in the liquid 3 in the dammed-up fluid serves for the gas-tight encapsulation of the discharge outlet 12 for the fermentation residues. The discharge outlet 12 for the fermentation residues is thus found underneath liquid level 25.

In addition, FIG. 6 shows an overview diagram of a liquefying plant 26. The liquefying of solids 2 takes place in fermenter 1. For this purpose, organic solids 2 and the liquid 3 of the dammed-up fluid are introduced into fermenter 1. Solids 2 can be discharged from fermenter 1 as solid fermentation residues 13. If needed, the solid fermentation residues 13 can be introduced again into fermenter 1. The liquid 3 in the dammed-up fluid and the fermentation gases 16 that form in fermenter 1 can also be returned again to fermenter 1. It is also possible, however, that the liquid 3 in the dammed-up fluid is pumped into another fermenter 1-1 for liquid and from there again reaches fermenter 1 or is discharged from the process.

The final products of the method can be stored.

LIST OF REFERENCE NUMBERS

1 Fermenter
1-1 Liquid fermenter
2 Solids
3 Liquid or dammed-up fluid containing the liquid
4 Solids inlet
5 Solids storage container
6 Conveyor device
6-1 Feed screw conveyor
7 Liquid inlet
8 Liquid discharge outlet
9 Stirrer
10 Shaft
11 Pressure and feed screw conveyor
12 Discharge outlet for the fermentation residues
13 Solid fermentation residues
14 Sieve
14-1 Lamella-type sieve with openings
14-2 Sieve of the pressure and feed screw conveyor
15 Gas discharge
16 Fermentation gas
17 Immersed pipe
18 Fermenter wall
19 Sleeve
20 Siphon
21 Fermenter bottom
22 Gas inlet
23 Gas distributor pipe
24 Opening
25 Liquid level
26 Liquefying plant

The invention claimed is:

1. A method for the continuous liquefying of organic solids, the method comprising the steps of: (a) providing:
(i) a fermenter having arranged therein:
first and second inlets in a lower region of the fermenter for introducing into said lower region a flow of liquid and/or an organic solids biomass;
first and second outlets in an upper region of the fermenter;
sieves positioned in an upper region of the fermenter and configured for:
(1) damming-up a biomass fluid, wherein said biomass in said fluid is an organic solids biomass subjected to enzymatic or microbial liquefying in the lower region;
(2) separating a portion of the liquids and dissolved gases in said dammed-up fluid by directing the liquids and dissolved gases through said sieves into an upper sieved region, and discharging the sieved liquids and dissolved gases out through the first outlet;
(3) directing the liquid-separated solid material retained in the dammed-up fluid by the sieves by flowing the liquid-separated solid material into said second outlet wherein the second outlet is a residue discharge outlet;
(ii) said liquid, consisting essentially of water and enriched with fermentation residual substances; and
(iii) said organic solids biomass; (b) introducing into the lower region of the fermenter the liquid and the organic solids biomass through said first and/or second inlets, and a microorganism or enzyme, thereby forming said biomass fluid; (c) incubating the biomass fluid for a residence time and under reaction conditions sufficient for microbially or enzymatically liquefying the organic solids biomass contained therein and at a biomass fluid through-flow rate through said fermenter sufficient for continuous liquefying of the organic solids biomass therein, thereby producing in the lower region of the fermenter a solid fermentation residue portion and a dissolved decomposition liquid and/or gas portion, the biomass fluid damming up against the sieves and said dissolved decomposition liquid and/or gas portion passing through said sieves into the upper sieved region; (d) collecting the solid fermentation residue portion in an upper region of the fermenter below a liquid surface level of the dammed-up fluid;

(e) removing the collected solid fermentation residue portion from the fermenter through said residue discharge outlet, thereby separating the collected solid fermentation residues from the liquid portion of the incubated dammed-up fluid; and (f) discharging from the fermenter the sieved liquid and dissolved gas portion.

2. The method according to claim 1, further comprising introducing the organic solids biomass below the liquid surface level in the fermenter.

3. The method according to claim 1, further comprising introducing the organic solids biomass into the fermenter by a liquid-impermeable conveyor device.

4. The method according to claim 1, further comprising introducing the organic solids biomass into the fermenter by a conveyor device, which has a conveyance path that begins above the liquid surface level of the fermenter.

5. The method according to claim 1, further comprising introducing the organic solids biomass into the fermenter by mechanical, hydraulic or pneumatic conveyance methods.

6. The method according to claim 1, further comprising spreading out the organic solids biomass in the lower region of the fermenter.

7. The method according to claim 1, further comprising removing the solid fermentation residue portion by a pressure and/or feed screw conveyor.

8. The method according to claim 1, further comprising guiding the solid fermentation residue portion by a solids scraper into a downpipe or a shaft.

9. The method according to claim 1, wherein the removing of step (e) further comprises producing an under pressure at a position in the fermenter where the solid fermentation residue portion is removed.

10. The method according to claim 1, further comprising circulating one or more portions selected from the group consisting of a portion of the discharged sieved liquid, a portion of the solid fermentation residue portion and/or a portion of the discharged fermentation gas by introducing said one or more portions of said discharged liquid, solid, or gas portions back into the fermenter from which said one or more portions were discharged and wherein said fermenter is a first fermenter, into a second fermenter, or into several fermenters.

11. The method according to claim 10, further comprising transferring the discharged liquid from the first fermenter into the second fermenter and then back into the first fermenter.

12. The method according to claim 10, further comprising in said second fermenter producing from the discharged liquid fermentation gas containing methane and/or hydrogen and returning said methane- and/or hydrogen-containing fermentation gas to the first fermenter.

13. The method according to claim 10, further comprising again transferring the discharged solid fermentation residue portion back to the first fermenter or guiding the discharged solid fermentation residue portion from said first fermenter to the second fermenter.

14. The method according to claim 1, further comprising introducing trace elements into the fermenter.

* * * * *